(12) United States Patent
Baban et al.

(10) Patent No.: US 9,625,445 B2
(45) Date of Patent: Apr. 18, 2017

(54) COMPOSITIONS AND METHODS FOR DIAGNOSING AND TREATING SJOGREN'S SYNDROME

(71) Applicant: Augusta University Research Institute, Inc., Augusta, GA (US)

(72) Inventors: Babak Baban, Augusta, GA (US); Mahmood Mozaffari, Martinez, GA (US); Rafik Abdelsayed, Augusta, GA (US); Jun Yao Liu, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 14/258,124

(22) Filed: Apr. 22, 2014

(65) Prior Publication Data
US 2014/0314715 A1   Oct. 23, 2014

Related U.S. Application Data

(60) Provisional application No. 61/814,544, filed on Apr. 22, 2013.

(51) Int. Cl.
| | |
|---|---|
| *C12Q 1/00* | (2006.01) |
| *G01N 33/48* | (2006.01) |
| *G01N 33/53* | (2006.01) |
| *G01N 33/00* | (2006.01) |
| *G01N 33/50* | (2006.01) |
| *A61K 38/18* | (2006.01) |

(52) U.S. Cl.
CPC ......... *G01N 33/5008* (2013.01); *A61K 38/18* (2013.01); *G01N 2500/04* (2013.01); *G01N 2800/24* (2013.01)

(58) Field of Classification Search
None
See application file for complete search history.

(56) References Cited

PUBLICATIONS

Chen et al. Biomarkers for Primary Sjogren's Syndrome. Genomics Proteomics Bioinformatics. 2015, 13:219-223.*
Hjelmervik et al. The minor salivary gland proteome in Sjögren's syndrome. Oral Diseases, 2009; 15(5):342-353.*
Abdulahad, et al., "Immune regulation and B-cell depletion therapy in patients with primary Sjögren's syndrome", J. Autoimmun., 39(1-2):103-11 (2012).
Atkinson, et al., "Cytotoxic T lymphocyte-assisted suicide. Caspase 3 activation is primarily the result of the direct action of granzyme B", J Biol Chem, 273:21261-6 (1998).
Baban, et al., "Aryl hydrocarbon receptor agonist, leflunomide, protects the ischemic-reperfused kidney: role of Tregs and stem cells", Am J Physiol Regul Integr Comp Physiol., 303(11:R1136-46 (2012a).
Baban, et al., "Endoplasmic reticulum stress response and inflammatory cytokines in type 2 diabetic nephropathy: role of indoleamine 2,3-dioxygenase and programmed death-1", Exp Mol Pathol., 94(2)343-51(2012b).
Baban, at al., "Pressure overload regulates expression of cytokines, $^{3}$H2AX, and growth arrest- and DNA-damage inducible protein 153 via glycogen synthase kinase-$3^{2}$ in ischemic-reperfused hearts", Hypertension., 61(1):95-104 (2013).
Brennan and Fuller, "Rapid upregulation of serum and glucocorticoid-regulated kinase (sgk) gene expression by corticosteroids in vivo", Mole Cell Endocrinology, 166:129-36 (2000).
Brenner, et al., "Physiological roles of the permeability transition pore", Circ Res., 111(9):1237-47 (2012).
Chavakis, et al., "Leucocyte recruitment in inflammation and novel endogenous negative regulators thereof", Eur J Clin Invest., 42(6):686-91 (2012).
Choi, et al., "Inhibition of leukocyte adhesion by developmental endothelial locus-1 (del-1)", Immune Netw., 9(5):153-7 (2009).
Cunard, "The endoplasmic reticulum stress response and diabetic kidney disease", Am. J. Physiol. Renal. Physiol., 300:F1054-61 (2011).
Darmon, et al., "Cleavage of CPP32 by granzyme B represents a critical role for granzyme B in the induction of target cell DNA fragmentation", J Biol Chem, 271:21709-12 (1996).
Eskan, et al., "The leukocyte integrin antagonist Del-1 inhibits IL-17-mediated inflammatory bone loss", Nat Immunol., 13(5):465-73 (2012).
Hasnain, et al., "The interplay between endoplasmic reticulum stress and inflammation", Immunol. Cell. Biol., 90:260-70 (2012).
Johnson, et al., "Stressed to death: targeting endoplasmic reticulum stress response induced apoptosis in gliomas", Curr Pharm Des., 17:284-92 (2012).
Khader, "Restraining IL-17: Del-1 deals the blow", Nat Immunol., 13(5):433-5 (2012).
Lauer, et al., "Differentiated murine airway epithelial cells synthesize a leukocyte-adhesive hyaluronan matrix in response to endoplasmic reticulum stress", J Biol Chem., 283(38):26283-96 (2008).
Liu, et al., "Apoptosis induced by endoplasmic reticulum stress involved in diabetic kidney disease", Biochem. Biophys. Res. Commun., 370:651-6 (2008).
Majors, et al., "Endoplasmic reticulum stress induces hyaluronan deposition and leukocyte adhesion", J Biol Chem, 278(47):47223-31 (2003).
Manoussakis, et al., "The role of epithelial cells in the pathogenesis of Sjögren's syndrome", Clin Rev Allergy Immunol, 32(3):225-30 (2007).

(Continued)

*Primary Examiner* — Vanessa L Ford
*Assistant Examiner* — Sandra Dillahunt
(74) *Attorney, Agent, or Firm* — Smith, Gambrell & Russell, LLP

(57) ABSTRACT

Methods for detection and diagnosis of Sjögren's Syndrome in a subject, determining the stage or progression of Sjögren's Syndrome in a subject, determining the effectiveness of a treatment for Sjögren's Syndrome, and selecting a subject for treatment for Sjögren's Syndrome are disclosed. The methods typically include measuring the level of one or more Sjögren's Syndrome biomarkers in a biological sample obtained from a subject. Biomarkers for Sjögren's Syndrome include, but are not limited to, GADD153 and Del-1.

5 Claims, 7 Drawing Sheets

(56) References Cited

PUBLICATIONS

Mathews, et al., "Oral manifestations of Sjögren's syndrome", J Dent Res, 87 (4): 308-318 (2008).

Miyazaki, et al., "C/EBP homologous protein deficiency attenuates myocardial reperfusion injury by inhibiting myocardial apoptosis and inflammation", Arterioscler Thromb Vasc Biol, 31(5):1124-32 (2011).

Mondal, et al., "Effect of endoplasmic reticulum stress on inflammation and adiponectin regulation in human adipocytes", Metab. Syndr. Relat. Disord., 10:297-306 (2012).

Moriyama, et al., "Cytokine/chemokine profiles contribute to understanding the pathogenesis and diagnosis of primary Sjögren's syndrome", Clin Exp Immunol., 169(1):17-26 (2012).

Mozaffari, et al., "Submandibular gland and caries susceptibility in the obese Zucker rat", J Oral Pathol Med., 40(2):194-200 (2011).

Mozaffari, et al., "Taurine in submandibular gland of the rat: effect of muscarinic drugs", J Histochem Cytochem., 50(4):527-32 (2002).

Ozcan, et al., "Chemical chaperones reduce ER stress and restore glucose homeostasis in a mouse model of type 2 diabetes", Science, 313:1137-40 (2006).

Ozcan, et al., "Endoplasmic reticulum stress links obesity, insulin action, and type 2 diabetes", Science, 305:457-61 (2004).

Pijpe, et al., "Parotid gland biopsy compared with labial biopsy in the diagnosis of patients with primary Sjogren's syndrome", Rheumatology, 46(2):335-441 (2007).

Roescher, et al., "Temporal changes in salivary glands of non-obese diabetic mice as a model for Sjögren's syndrome", Oral Dis., 18(1):96-106 (2012).

Seror, et al., "Outcome measures for primary Sjögren's syndrome", J Autoimmun., 39(1-2):97-102 (2012).

Singh, et al., "The T cell in Sjogren's syndrome: force majeure, not spectateur", J Autoimmun., 39(3):229-33 (2012).

Tzioufas, et al., "Pathogenesis of Sjögren's syndrome: what we know and what we should learn", J Autoimmun., 39(1-2):4-8 (2012).

Varin, et al., "In Sjögren's syndrome, B lymphocytes induce epithelial cells of salivary glands into apoptosis through protein kinase C delta activation", Autoimmun Rev. 11(4):252-8 (2012).

Vianello, et al., "The mitochondrial permeability transition pore (PTP)—an example of multiple molecular exaptation", Biochim Biophys Acta., 1817 (11):2072-86 (2012).

Vladykovskaya, et al., "Lipid peroxidation product 4-hydroxy-trans-2-nonenal causes endothelial activation by inducing endoplasmic reticulum stress", J Biol Chem., 287(14):11398-409 (2012).

Waldegger, et al., "h-sgk serine-threonine protein kinase as transcriptional target of p30/MAP pathway in HepG2 human hepatoma cells", Cell Physiol Biochem., 10:203-8 (2000).

Waldegger, et al., "h-sgk serine-threonine protein kinase gene as transcriptional target of transforming growth factor$^2$ in human instestine", Gastroenterology, 116:1081-8 (1999).

Warntges, et al., "Cerebral localization and regulation of the cell volume-sensitive serum and glucocorticoid-dependent kinase SGK1", Pflugers Arch., 443:617-24 (2002).

* cited by examiner

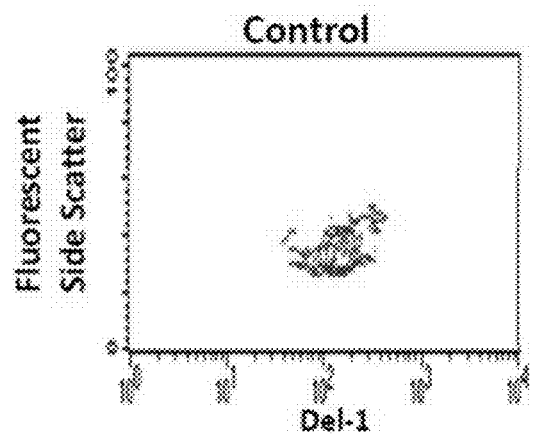
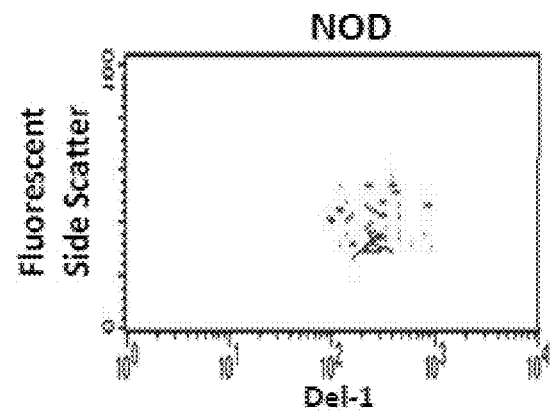
Fig. 2A  Fig. 2B
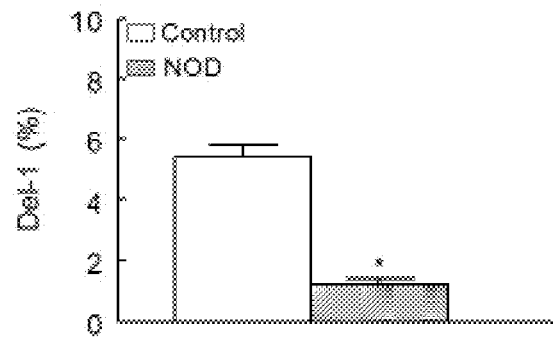
Fig. 2C

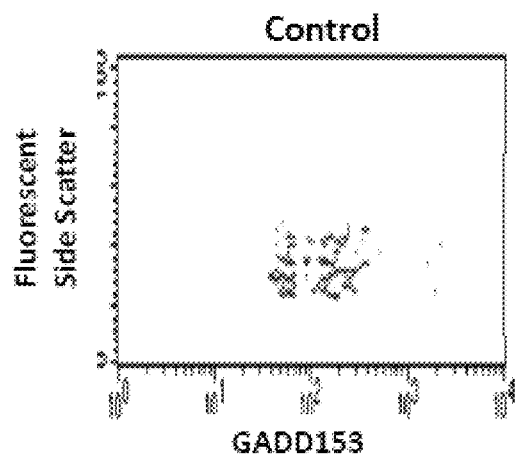
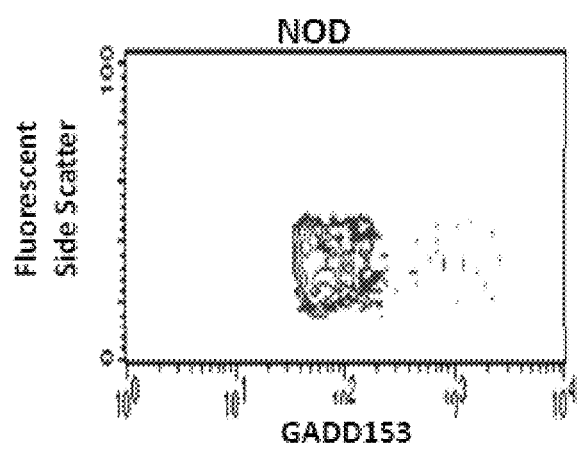
Fig. 3A    Fig. 3B
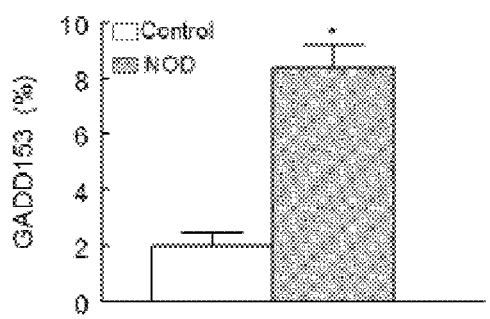
Fig. 3C

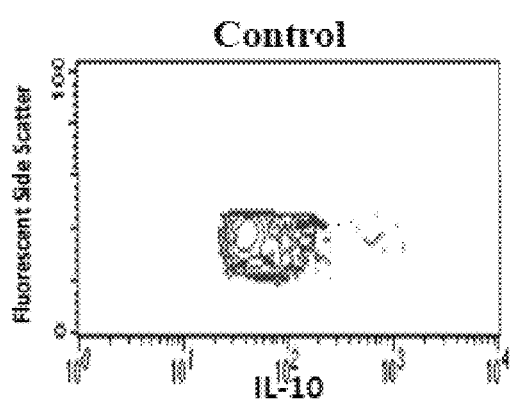 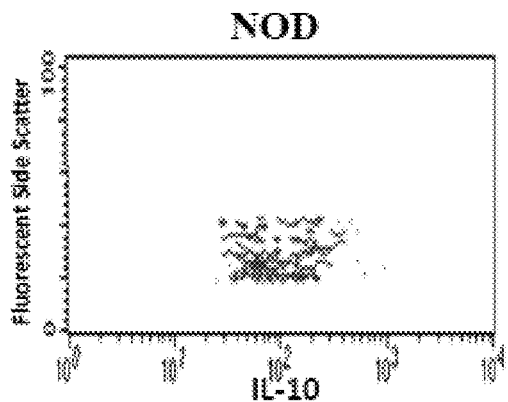
Fig. 5A  Fig. 5B
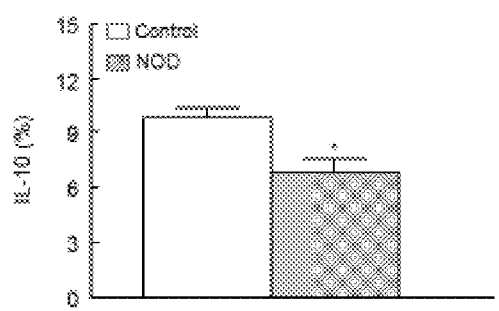
Fig. 5C

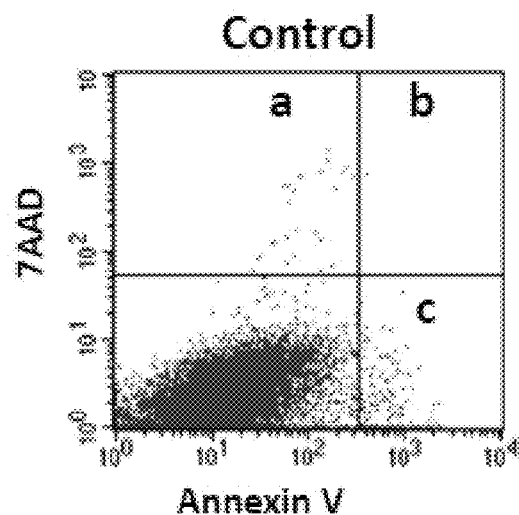
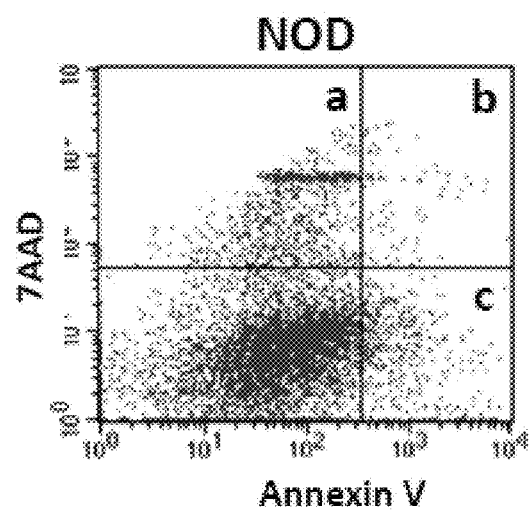
Fig. 7A
Fig. 7B
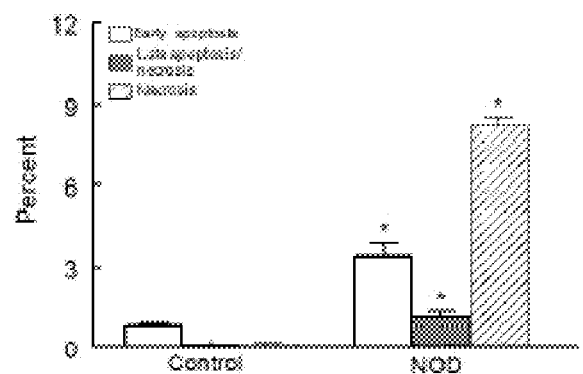
Fig. 7C

COMPOSITIONS AND METHODS FOR DIAGNOSING AND TREATING SJOGREN'S SYNDROME

CROSS-REFERENCE TO RELATED APPLICATIONS

This application claims priority to U.S. Provisional Application Ser. No. 61/814,544, filed Apr. 22, 2013. The disclosure of this application is incorporated herein by reference in their entirety.

FIELD OF THE INVENTION

This invention is generally related to biomarkers for Sjögren's Syndrome.

BACKGROUND OF THE INVENTION

Sjögren's Syndrome (SS) is a systemic autoimmune disease with a prevalence of 1-3%, affecting more women than men with a ratio of 9:1. It is characterized by chronic focal leukocyte infiltration and inflammation of exocrine glands, primarily involving salivary (and lacrimal) glands thereby resulting in persistence dryness of the mouth (and eyes). Primary SS occurs independent of another autoimmune disease while secondary SS occurs against a background of other connective tissue diseases (e.g., rheumatoid arthritis, systemic lupus erythematosus). The serological hallmark of SS is the presence of circulating autoantibodies against soluble nuclear RNA containing antigens, Ro/SSA and La/SSB (Tzioufas, et al., *J Autoimmun.*, 39(1-2):4-8 (2012); Seror, et al., *J Autoimmun.*, 39(1-2):97-102 (2012); Mathews, et al., *J Dent Res*, 87(4): 308-318 (2008)).

The pathogenesis of SS remains poorly understood but hallmark histopathological findings of the disease include perivascular and periductal leukocyte infiltration of exocrine glands and associated inflammation (Tzioufas, et al., *J Autoimmun.*, 39(1-2):4-8 (2012); Seror, et al., *J Autoimmun.*, 39(1-2):97-102 (2012); Mathews, et al., *J Dent Res*, 87(4): 308-318 (2008); Abdulahad, et al., *J. Autoimmun.*, 39(1-2): 103-11 (2012); Singh, et al., *J Autoimmun.*, 39(3:229-33 (2012); Roescher, et al., *Oral Dis.*, 18(1):96-106 (2012); Moriyama, et al., *Clin Exp Immunol.*, 169(1):17-26 (2012)). One potential mechanism for leukocyte infiltration could relate to dysregulation of recently discovered endogenous inhibitors of leukocyte adhesion. Prominent among them is the developmental endothelial locus-1 (Del-1) which has emerged as an important player in pathogenesis of several conditions including periodontitis (Chavakis, et al., *Eur J Clin Invest.*, 42(6):686-91 (2012); Choi, et al., *Immune Netw.*, 9(5):153-7 (2009); Eskan, et al., *Nat Immunol.*, 13(5):465-73 (2012)). Aside from the contribution of systemic immune and inflammatory mechanisms, mounting evidence supports a pivotal role for the endoplasmic reticulum (ER) stress response in regulating endogenous cellular inflammatory mechanisms and cell death (Johnson, et al., *Curr Pharm Des.*, 17, 284-292 (2012); Liu, et al., *Biochem. Biophys. Res. Commun.*, 370, 651-656 (2008); Mondal, et al., *Metab. Syndr. Relat. Disord.*, 10, 297-306 (2012); Cunard, *Am. J. Physiol. Renal. Physiol.*, 300, F1054-F1061 (2011); Baban, et al., *Hypertension*. 61(1):95-104 (2013); Baban, et al., *Exp Mol Pathol.*, doi:pii: S0014-4800(12) 00175-X. 10.1016/j.yexmp 0.2012.11.004 [Epub ahead of print] (2012); Miyazaki, et al., *Arterioscler Thromb Vasc Biol*, 31(5):1124-32 (2011); Hasnain, et al., *Immunol. Cell. Biol.*, 90, 260-70 (2012)). Importantly, the status of ER stress response and potential role of Del-1 in pathogenesis of salivary gland impairment in SS are not established.

Therefore, it is an objection of the invention to provide compositions and methods for detecting, diagnosing, and monitoring the progression of SS.

It is also an object of the invention to provide compositions and methods for treating SS.

It is a further object of the invention to provide methods of monitoring the effectiveness of SS treatment.

SUMMARY OF THE INVENTION

It has been discovered that endoplasmic reticulum (ER) stress response contributes importantly to salivary gland inflammation and cell death. Because salivary gland inflammation and salivary gland cell death are symptoms of Sjögren's Syndrome, modulating ER stress response in salivary and lacrimal glands is an effective method for treating subjects with Sjögren's Syndrome. In one embodiment, the method of treatment for Sjögren's Syndrome includes administering an effective amount of an agent to a subject in need thereof to increase expression of Del-1, decrease expression of GADD153 or both. In other embodiments, the method of treatment includes administering an effective amount of Del-1 to inhibit or reduce immune cell infiltration into salivary or lacrimal glands.

Methods for detection and diagnosis of Sjögren's Syndrome in a subject, determining the stage or progression of Sjögren's Syndrome in a subject, determining the effectiveness of a treatment for Sjögren's Syndrome, and selecting a subject for treatment for Sjögren's Syndrome are disclosed. The methods typically include measuring the level of one or more Sjögren's Syndrome biomarkers in a biological sample obtained from a subject. Biomarkers for Sjögren's Syndrome include, but are not limited to GADD153 and Del-1. An elevated level of the GADD153, a decreased level of Del-1, or both in the sample relative to a control is indicative of Sjögren's Syndrome. The level of the one or more biomarkers can also be compared to reference levels that correlate with disease severity or progression of Sjögren's Syndrome or to determine the stage or progression of the disease. In some embodiments, the method of detection, diagnosis, or disease progression includes a step of treating the subject for one or more symptoms of Sjögren's Syndrome.

Kits and devices for use in diagnosing and monitoring the subjects are also disclosed.

Methods for screening for agents useful for treating one or more symptoms of Sjögren's Syndrome are also provided. One embodiment provides method for screening for a compound for the treatment of one or more symptoms of Sjögren's Syndrome by administering the compound to a NOD mouse, determining the levels of Del-1 expression in salivary or lacrimal gland cells of the NOD mouse after administration of the compound, and selecting the compound that increases expression of Del-1 in the salivary or lacrimal gland cells of the NOD mouse.

BRIEF DESCRIPTION OF THE DRAWINGS

FIGS. 1A and 1B show cells stained for CD 19 (B cells) from the salivary tissue of control and NOD mice, respectively. FIGS.

1C and 1D show cells stained for CD3 (T cells) from the salivary tissues of control and NOD mice, respectively.

FIGS. 2A and 2B are scatter dot plots that show representative results of analytical flow cytometry, gated to exclude dead cells and debris, to visualize cells stained for Del-1 from the salivary tissue of control (FIG. 2A) and NOD (FIG. 2B) mice, respectively. In each analysis, 100,000 total events were collected, where each event represents a single cell or particle. FIG. 2C is a bar graph showing the percentage of cells immunostained for Del-1 in control and NOD mice, respectively. Bars are shaded according to the legend; data in the bar graph are means±SEM of n=5 mice/group. The asterisk indicates a statistically significant difference (p<0.05) compared to the control group.

FIGS. 3A and 3B are scatter dot plots that show representative results of analytical flow cytometry, gated to exclude dead cells and debris, to visualize cells stained for GADD153 from the salivary tissue of control and NOD mice, respectively. In each analysis, 100,000 total events were collected, where each event represents a single cell or particle. FIG. 3C is a bar graph showing percentage of cells immunostained for GADD153 in control and NOD mice, respectively. Bars are shaded according to the legend; data in the bar graph are means±SEM of n=5 mice/group. The asterisk indicates a statistically significant difference (p<0.05) compared to the control group.

FIGS. 5A and 5B are scatter dot plots that show representative results of analytical flow cytometry, gated to exclude dead cells and debris, to visualize cells stained for IL-10 from the salivary tissue of control and NOD mice, respectively. In each analysis, 100,000 total events were collected, where each event represents a single cell or particle. FIG. 5C is a bar graph showing the percentage of cells immunostained for IL-10 in control and NOD mice, respectively. Bars are shaded according to the legend; data in the bar graph are means±SEM of n=5 mice/group. The asterisk indicates a statistically significant difference (p<0.05) compared to the control group.

FIGS. 7A and 7B are scatter dot plots that show the results of analytical flow cytometry, plotting Annexin V (Y-axis) against 7-Amino-Actinomycin D (7-AAD; X-axis). Each plot shows the relative proportions of cells undergoing necrosis (panel a, top left), apoptosis/necrosis (panel b, top right), and early apoptosis (panel c, bottom right) amongst cells prepared from the submandibular glands of control (FIG. 7A) and NOD (FIG. 7B) mice, respectively. FIG. 7C is a bar graph showing the percentage of cells identified as undergoing necrosis, apoptosis/necrosis, and early apoptosis, amongst the two groups of control and NOD mice, respectively. Bars are shaded according to the legend; data in the bar graph are means±SEM of n=5 mice/group. The asterisks indicate a statistically significant difference (p<0.05) compared to the control group.

DETAILED DESCRIPTION OF THE INVENTION

I. Definitions

Figure 1A:
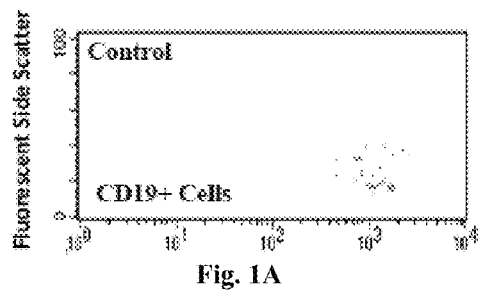
FIGS. 1A-1D are scatter dot plots that show representative results of flow cytometry to visualize cells from the salivary tissue of mice, gated to exclude dead cells and debris. In each analysis, 100,000 total events were collected, where each event represents a single cell or particle.

As used herein, "biological sample" refers to biological material isolated from a subject. The sample can contain any suitable biological material, but preferably comprises cells obtained from a particular tissue or biological fluid. In this respect, the sample can be blood, blood serum, plasma, or tissue. In a preferred embodiment, the sample is a biopsy tissue sample of a suspected tumor.

As used herein, "biomarker" refers to an organic molecule produced by an organism that is indicative or correlative of a disease state. Biomarkers include, but are not limited to proteins, metabolites, post-translationally modified proteins, etc.

As used herein, "subject" and "patient," and are used interchangeably and refer to any individual who is the target of analysis or treatment using the disclosed methods or compositions. The subject can be a vertebrate, for example, a mammal, such as a human. The subjects can be symptomatic or asymptomatic. The term does not denote a particular age or sex. Therefore, the subject can be an adult, child, or a newborn. The subject can be male or female. A subject can include a control subject or a test subject.

As used herein, "treating" includes alleviating the symptoms associated with a specific disorder or condition and/or preventing or eliminating those symptoms.

II. Biomarkers for Detecting or Diagnosing SjöGren's Syndrome

ER stress response and Del-1 contribute importantly to inflammation and salivary gland cell death in the SS-like condition of NOD mice. The data provided in the Examples shows that salivary glands of NOD mice display a) significant increase in GADD153 expression in association with increased γH2AX immunostaining, b) significant reduction in Del-1 expression in association with marked infiltration of immune cells including B and T lymphocytes as well as M1 and M2 macrophages, c) significant reduction in anti-inflammatory cytokine, IL-10, but marked increase in the pro-inflammatory cytokine, IL-17 and d) disruption of $\psi_m$ in association with significant increase in both apoptosis and necrosis accompanied with caspase 3 activation. The reciprocal relations between GADD153 and Del-1 as well as between Del-1 and IL-17 are suggestive of functional crosstalk between ER stress response and Del-1 in regulation of salivary gland inflammation. Importantly, lower lip biopsy samples of SS subjects displayed marked reduction in Del-1 but prominent increase in GADD153 compared to those of non-SS subjects. Collectively, these observations establish pivotal roles for GADD153 and Del-1 in pathogenesis of salivary gland inflammation in SS.

A. ER Stress Response

The unfolded protein response (UPR) is a normal homeostasis response which allows the cell to cope with stressful conditions associated with increased unfolded/misfolded protein loads. Mammalian cells possess three major arms of the UPR which ultimately lead to downregulation of protein translation but transcription of genes including those for ER chaperones and ER associated degradation proteins (Johnson, et al., *Curr Pharm Des.*, 17, 284-292 (2012); Liu, et al., *Biochem. Biophys. Res. Commun.*, 370, 651-656 (2008); Mondal, et al., *Metab. Syndr. Relat. Disord.*, 10, 297-306 (2012); Cunard, *Am. J. Physiol. Renal. Physiol.*, 300, F1054-F1061 (2011); Baban, et al., *Hypertension*. 61(1):95-104 (2013); Baban, et al., *Exp Mol Pathol.*, doi:pii: S0014-4800(12)00175-X. 10.1016/j.yexmp.2012.11.004 [Epub ahead of print] (2012); Miyazaki, et al., *Arterioscler Thromb Vasc Biol*, 31(5):1124-32 (2011)). These processes provide the opportunity for the protein folding machinery of the ER to catch up with the backlog of unfolded proteins. Failure of the UPR mechanism is referred to as the ER stress response which describes a condition whereby a stressful stimulus has exhausted or markedly disrupted the capacity of the ER for protein folding.

Thus, failure of survival attempts is associated with the ER stress response eliciting a final maneuver culminating in apoptosis (Johnson, et al., *Curr Pharm Des.*, 17, 284-292 (2012); Liu, et al., *Biochem. Biophys. Res. Commun.*, 370, 651-656 (2008); Cunard, *Am. J. Physiol. Renal. Physiol.*, 300, F1054-F1061 (2011)). An integral component of ER stress-induced apoptosis is expression of C/EBP homologue protein (CHOP or GADD153) which is normally present in low levels but its expression markedly increases following severe/sustained stress to the ER.

mitochondrial death pathway (23-27).

B. GADD153

GADD153 is a component of DNA damage response and a signaling event that underlies ER stress-induced apoptosis (15-16, 17). Likely mechanisms for GADD153-induced apoptosis include induction of cellular oxidative stress and subsequent mobilization of the Importantly, however, GADD153 has also emerged as a modulator of the inflammatory response (Chavakis, et al., *Eur J Clin Invest.*, 42(6): 686-91 (2012); Miyazaki, et al., *Arterioscler Thromb Vasc Biol*, 31(5):1124-32 (2011)). Indeed, the ER stress response plays an important role in a number of pathological conditions associated with chronic inflammation including diabetes mellitus/insulin resistance (Ozcan, et al., *Science*, 313, 1137-1140 (2006); Ozcan, et al., *Science*, 305, 457-461 (2004)).

A major finding is the demonstration that salivary glands of NOD mice display increased γH2AX immunostaining (a marker of the most severe DNA damage, double stand DNA breaks; 15) and marked increase in GADD153 expression suggestive of an important role for ER stress response in the pathogenesis of SS. Upregulation of ER stress response in salivary tissue of NOD mice is consistent with the pivotal role of salivary gland epithelial cells in contributing to the inflammation of the salivary glands in SS (Manoussakis, et al., *Clin Rev Allergy Immunol*, 32(3):225-30 (2007)). Indeed, salivary gland epithelial cells in SS are well-recognized as orchestrators and major contributors to the autoimmune and inflammatory processes through elaborations of a whole host of immunecompetent molecules implicated in the innate and adaptive immune response. The recognition of the pivotal role of epithelial cells in salivary gland inflammation has led to the "epitheliocentric" pathogenic model which incorporates the multifaceted contributions of epithelial cells (Manoussakis, et al., *Clin Rev Allergy Immunol*, 32(3):225-30 (2007)).

The marked increase in GADD153 expression of salivary glands (e.g., ductal cells) is consistent with endogenous upregulation of inflammatory mechanisms in salivary glands in the setting of SS. Indeed, salivary gland of NOD mice displayed marked increased in IL-17 but reduction in IL-10. Importantly, upregulation of IL-17 was more marked than the reduction in IL-10 expression suggestive of the prominent role of pro-inflammatory cytokines in this condition. Further, the demonstration of expression of these cytokines in salivary gland ductal cells is consistent with their expressions in other cells including cardiac and kidney cells in other conditions (Baban, et al., *Hypertension*. 61(1):95-104 (2013); Baban, et al., *Exp Mol Pathol.*, doi:pii: S0014-4800(12)00175-X. 10.1016/j.yexmp.2012.11.004 [Epub ahead of print] (2012); Baban, et al., *Am J Physiol Regul Integr Comp Physiol.*, 303(11:R1136-46 (2012)).

C. Del-1

Aside from direct contribution of salivary gland epithelial cells to inflammation, perivascular and periductal leukocyte infiltration is a well-recognized hallmark feature and contributor to salivary gland abnormalities of SS. The process of leukocyte recruitment is a highly regulated cascade of adhesive interactions between the endothelium and leukocytes involving a whole host of factors including adhesion molecules, selectins and integrins among others (Chavakis, et al., *Eur J Clin Invest.*, 42(6):686-91 (2012); Choi, et al., *Immune Netw.*, 9(5):153-7 (2009); Eskan, et al., *Nat Immunol.*, 13(5):465-73 (2012)). Importantly, the accumulation of leukocytes in tissues could result in significant release of cytotoxic mediators leading to tissue injury and a wide spectrum of inflammatory conditions (as it occurs in SS). Thus, effective inhibition of excessive or misdirected leukocyte recruitment provides a means for curtailing inflammation.

Recent studies have identified endogenous inhibitors of leukocyte adhesion. Foremost among them is the developmental endothelial locus-1 (Del-1) also known as Edil3 (Choi, et al., *Immune Netw.*, 9(5):153-7 (2009)). Del-1 is a 53 kDa glycoprotein which is secreted by the endothelial cells and associates with the endothelial cell surface and extracellular matrix. Del-1 expression was initially observed in embryonic cells including endothelial cells and thymus and subsequently shown in adult endothelial cells and some subsets of macrophages (Choi, et al., *Immune Netw.*, 9(5): 153-7 (2009)). More recent studies have established that Del-1 is expressed in adult mice in a tissue-specific manner with strong expression in the brain, eye and lung. Del-1 is shown to function as an endogenous inhibitor of a major leukocyte adhesion receptor, namely LFA-1, to suppress leukocyte adhesion to the endothelium and entry to inflamed tissues (Eskan, et al., *Nat Immunol.*, 13(5):465-73 (2012); Eskan, et al., *Nat Immunol.*, 13(5):465-73 (2012)). Importantly, salivary glands of NOD mice display a marked reduction in expression of Del-1 thereby offering a plausible explanation for the marked leukocyte accumulation in the tissue which we have shown to include B and T lymphocytes as well as M1 and M2 macrophages. Indeed, Del-1 is shown to play an important role in leukocyte trafficking in other pathologies including periodontitis (Eskan, et al., *Nat Immunol.*, 13(5):465-73 (2012)). Interestingly, B cells and M2 macrophages were more prominent than T cells and M1 macrophages, the functional significance of which remains to be explored in light of the temporal relation of immune cell infiltrates in salivary glands in SS (Roescher, et al., *Oral Dis.*, 18(1):96-106 (2012)). Nonetheless, the observation that reduction in Del-1 expression is accompanied by significant increase in GADD153 expression is suggestive of potential regulation of Del-1 expression by ER stress response. Interestingly, increased ER stress response promotes leukocyte adhesion to endothelium (Lauer, et al., *J Biol Chem.*, 283(38):26283-96 (2008); Vladykovskaya, et al., *J Biol Chem.*, 287(14):11398-409 (2012); Majors, et al., *J Biol Chem,* 278(47):47223-31 (2003)). Thus, the reciprocal relation between GADD153 and Del-1 in this study suggests a mechanistic link between ER stress response and leukocyte infiltration into the salivary glands of NOD mice, a model of SS-like disease. Importantly, Del-1 is also shown to inhibit IL-17 expression in a model of periodontitis (Eskan, et al., *Nat Immunol.*, 13(5):465-73 (2012); Khader, *Nat Immunol.*, 13(5):433-5 (2012)). Thus, the observation that Del-1 is reduced in salivary gland of NOD mice is consistent with the marked upregulation of IL-17 expression. A pro-inflammatory environment can be conducive to cell death of the affected organ. Further, loss of epithelial cells of salivary glands (e.g., via apoptosis) is known to accompany the development and progression of SS. The proposed mechanisms of apoptosis of salivary gland epithelial cells include a) intrinsic activation of epithelial cells by membrane folding through autocrine Fas/FasL interactions, b) interaction of epithelial cells with infiltrating/neighboring T lymphocytes thereby undergoing apoptosis and c) release of granular factors (e.g., perforine and granzyme B) from activated cytotoxic CD4+ and CD8+ T lymphocytes culminating in activation of the caspase cascade (Khader, *Nat Immunol.*, 13(5):433-5 (2012); Darmon, et al., *J Biol Chem,* 271:21709-12 (1996); Atkinson, et al., *J Biol Chem,* 273: 21261-6 (1998)). Interestingly, a recent report also suggests contribution of B lymphocytes to epithelial cell apoptosis (Varin, et al., *Autoimmun Rev.* 11(4):252-8 (2012)). Thus, the contribution of infiltrating B and T lymphocytes into the salivary gland tissue in relation to epithelial cell apoptosis is well-founded.

D. Biomarkers of Apoptosis

In light of the demonstration of marked increase in GADD153 expression and the proinflammatory environment of salivary glands of NOD mice, cell death was examined in the context of assessment of $\psi_m$. Aside from production of ATP via oxidative phosphorylation for a variety of cellular functions, the mitochondria can initiate cell death through both apoptosis and necrosis under severe stressful conditions. Mitochondrial-mediated cell death ensues following opening of the MPT pore, in the mitochondrial inner membrane, thereby causing swelling of the matrix and ultimately leading to the rupture of the mitochondrial outer membrane thereby releasing pro-apoptotic proteins into the cytoplasm. For example, induction of MPT pore results in subsequent release of cytochrome c which, in turn, causes activation of the caspase cascade, eventually, causing cell death (Baban, et al., *Hypertension.* 61(1):95-104 (2013); Baban, et al., *Exp Mol Pathol.*, doi:pii: S0014-4800(12)00175-X. 10.1016/j.yexmp.2012.11.004 [Epub ahead of print] (2012); Baban, et al., *Am J Physiol Regul Integr Comp Physiol.*, 303(11:R1136-46 (2012); Brenner, et al., *Circ Res.*, 111(9):1237-47 (2012); Vianello, et al., *Biochem Biophys Acta.*, 1817(11):2072-86 (2012)). Consistent with these observations, the data in the Examples show reduced JC-1 aggregates but increased JC-1 monomers of cells prepared from salivary glands of NOD than control mice suggestive of disruption of $\psi_m$. Loss of $\psi_m$ is associated with opening of the MPT pore and ensuing cell death via apoptosis and necrosis (Baban, et al., *Hypertension.* 61(1):95-104 (2013); Hasnain, et al., *Immunol. Cell. Biol.,* 90, 260-70 (2012); Baban, et al., *Am J Physiol Regul Integr Comp Physiol.*, 303(11:R1136-46 (2012)). The results revealed significant increase in disruption of $\psi_m$ accompanied with significant increase in both apoptosis and necrosis. GADD153-induced apoptosis is suggested to transcriptionally regulate genes that participate in the apoptotic pathway (Johnson, et al., *Curr Pharm Des.*, 17, 284-292 (2012)). The increase in GADD153 is associated with indirect inhibition of Bcl2 expression and subsequent unleashing of the apoptotic triggering effect of Bax/Bad systems in the mitochondria, resulting in caspase 9 and then caspase3 activation. Further, activated or cleaved caspase-3 is emerging as the molecular biomarker/verification of the apoptotic process and complements assessment of Annexin V (Johnson, et al., *Curr Pharm Des.*, 17, 284-292 (2012); Baban, et al., *Exp Mol Pathol.*, doi:pii: S0014-4800(12)00175-X. 10.1016/j.yexmp.2012.11.004 [Epub ahead of print] (2012)). Indeed, salivary glands of NOD mice displayed intense immunostaining for caspase 3 in association with apoptosis.

E. GADD153 and Del-1 Expression in Subjects with SS

In light of the reciprocal relation between GADD153 and Del-1 expressions in salivary gland of NOD mice, the relevance of these novel observations were explored for the human condition. Assessment of leukocyte infiltration into minor salivary glands of lower lip biopsy samples in commonly used to aid with diagnosis of SS; however, this approach may identify 60% of those afflicted with the disease thereby requiring use of additional diagnostic tests/markers (Pijpe, et al., *Rheumatology,* 46(2):335-441 (2007)). Interestingly, lower lip biopsy samples of SS subjects displayed marked reduction in Del-1 expression but intense expression of GADD153 compared to those of non-SS subjects. The remarkable similarity in expression patterns of GADD153 and Del-1 in minor salivary glands of SS subjects and the major salivary glands of NOD mice not only reinforces the relevance of NOD mice as an animal of SS but also highlights the potential predictive diagnostic value of these molecules as molecular fingerprints of SS.

In conclusion, a pivotal role for ER stress response, as indexed by increased GADD153 expression, in salivary gland inflammation and cell death in the setting of SS-like disease in NOD mice has been discovered. Importantly, a marked decrease in Del-1 accompanies leukocyte infiltration and upregulation of GADD153. Since ER stress response is implicated in leukocyte adhesion, our collective findings suggest a mechanistic link between GADD153 and Del-1 in regulation of salivary gland inflammation in SS. Importantly, utilizing lower lip biopsy samples of SS subjects we have established the relevance of GADD153 and Del-1 for the human condition. While this study focused on salivary glands, the demonstration of the link between GADD153 and Del-1 is of relevance and significance for other target organs impacted by SS.

III. Methods of Using Biomarkers for Detecting, Diagnosing Sjögren's Syndrome

One or more of the biomarkers disclosed herein can be used to detect, diagnose, or monitor progression of Sjögren's Syndrome. The methods typically include detecting one or more of the biomarkers in a biological sample obtained from the subject and comparing it to a control or reference levels.

In some embodiments, the presence of or an increase in the biomarker compared to the control is indicative that subject has Sjögren's Syndrome. An exemplary biomarker that has increased expression in Sjögren's Syndrome is GADD153.

In other embodiments, the decrease in the biomarker in salivary or lacrimal gland cells compared to the control is indicative that subject has Sjögren's Syndrome. An exemplary biomarker that has decreased expression in Sjögren's Syndrome is Del-1.

In still another embodiment, an increase in GADD153 expression with a concomitant decrease in Del-1 expression in salivary or lacrimal gland cells of a subject is indicative of Sjögren's Syndrome.

The methods can include any number of additional detection, diagnostic, staging, or progression monitoring steps that are known in the art. Other histological, hematological, immunological, biochemical, metabolic, etc., methods can be employed in combination with the disclosed methods to increases the accuracy or precision of the diagnosis. Additional diagnostic steps may include a complete blood count, a complete chemistry panel (including alkaline phosphatase, hepatic transaminases, total protein, and albumin), lactate dehydrogenase assay, chest radiography, magnetic resonance imaging, ultrasonography, computed tomography, positron emission tomography, complete excisional biopsy of a suggestive lesion, surgical excision or reexcision after biopsy, elective lymph node dissection (ELND), sentinel lymph node biopsy (SLNB).

A. Methods of Detection

1. Biological Samples

A biological sample can be obtained from an individual for use in the methods and bioassays disclosed herein. In some embodiments, the sample is a tissue biopsy or cells obtained from the subject. The sample should be handled in accordance with the method of detection that will be employed. In some embodiments, a biological sample that is of tissue or cellular origin can be solubilized in a lysis buffer optionally containing a chaotropic agent, detergent, reducing agent, buffer, and salts. The conditions for handling biological samples that are analyzed for mRNA level may be different than the conditions for handling biological samples that are analyzed for protein level, and such conditions are known in the art.

In preferred embodiments, the biological sample is a tissue sample that includes salivary or lacrimal gland cells. The biological sample may be a biopsy. Methods for performing biopsies are known in the art and include:

Fine Needle Aspirate (FNA)—a technique in which a needle is inserted into the tissue to aspirate (take out) fluid and cells. This tissue/fluid can smeared onto a slide for subsequent analysis.

Shave Biopsy—a technique in which tissue is cut off the surface of the skin.

Punch Biopsy—a technique in which cells or tissue are removed from the skin using a cookie cutter type device.

Incisional Biopsy—a technique in which cells or tissue are removed from the skin by cutting out the affected area.

Excisional Biopsy—a technique in which tissue is removed from the skin by cutting out the affected area as well as a portion of normal skin surrounding the lesion.

Examples of other biological samples include urine, barbotage, blood, serum, plasma, tears, saliva, cerebrospinal fluid, tissue, lymph, synovial fluid, or sputum etc. Serum is the component of whole blood that is neither a blood cell (serum does not contain white or red blood cells) nor a clotting factor. It is the blood plasma with the fibrinogens removed. Accordingly, serum includes all blood proteins not used in blood clotting (coagulation) and all the electrolytes, antibodies, antigens, hormones, and any exogenous substances (e.g., drugs and microorganisms). The sample can be diluted with a suitable diluent before the sample is analyzed.

2. Methods of Detection a. Detecting Gene Products

If the biomarker is a gene product such as GADD153 or Del-1, the biomarker can be detected by analyzing the level of mRNA or protein in a biological sample obtained from a subject. Conventional methods for detecting mRNA and protein are known in the art and can be cell-based or cell-free assays.

For example, mRNA levels can be determined using assays, including, but not limited to, RT-PCR, reverse transcription real-time PCR(RT-qPCR), transcriptome analysis using next-generation sequencing, array analysis, digital PCR, and northern analysis. In a preferred embodiment, the method includes detecting the level of GADD153, Del-1 mRNA, or a combination thereof in mRNA isolated from cells of the subject. In some embodiments, a probe for detecting GADD153, Del-1 mRNA is designed to hybridize with the nucleic acid sequence of GADD153, Del-1 mRNA, respectively.

b. Detecting Proteins

Protein expression can be detected using routine methods, such as immunodetection methods, mass spectroscopy, or high performance liquid chromatography (HPLC). In a preferred embodiment, the method includes detecting the level of GADD153 protein or polypeptide, Del-1 protein or polypeptide, or a combination thereof in cells, or tissue of the subject.

A preferred method includes immunoassays whereby polypeptides of the biomarker are detected by their interaction with a biomarker specific antibody. For example, if the biomarker is GADD153 or Del-1, the antibody or antibodies used in the assay is specific for GADD153 or Del-1, respectively. The biomarker can be detected in either a qualitative or quantitative manner. Exemplary immunoassays that can be used for the detection of biomarker polypeptides and proteins include, but are not limited to, radioimmunoassays, ELISAs, immunoprecipitation assays, Western blot, fluorescent immunoassays, and immunohistochemistry, flow cytometry, protein arrays, multiplexed bead arrays, magnetic capture, in vivo imaging, fluorescence resonance energy transfer (FRET), and fluorescence recovery/localization after photobleaching (FRAP/FLAP). It will be appreciated that some immunoassays, for example ELISAs, can require two different biomarker specific antibodies.

Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip® array.

In a preferred embodiment, GADD153, Del-1, or a combination thereof are detected using immunohistochemical or immunofluorescent staining of a cell smear or tissue sample obtained from the subject.

3. Controls

The methods disclosed herein typically including comparing the level of the biomarker detected in a sample obtained from the subject to a control. Suitable control will be known to one of skill in the art. For example, controls can include, standards obtained from healthy subjects, such as subjects without Sjögren's Syndrome. Reference indices can be established by using subjects that have been diagnosed with Sjögren's Syndrome with different known disease severities or prognoses. A control can be a single or more preferably pooled or averaged values of like individuals using the same assay.

In some embodiments, the control biological sample is assayed using the sample methods as the test sample.

B. Methods of Monitoring Disease Progression

In some embodiments, the methods of detection, diagnosis, and staging are used to monitor disease progression. Typically, the methods of monitoring disease progression include measuring the level of one or more of the disclosed biomarkers in biological samples taken at a first time point and a second time point. Typically the two biological samples are taken from the same source, tissue, or location. For example, one or more biomarkers such as GADD153 or Del-1 can be measure in a first biological sample at a first time point, and later measured in a second biological sample at a second time point. Presence of or increase of GADD153 and the decrease of Del-1 at the second time point compared to the first time point is indicative that the Sjögren's Syndrome has increased in severity. Absence of, or decrease of GADD153 and an increase in Del-1 at the second time point compared to the first time point is indicative that the Sjögren's Syndrome has decreased in severity. No change in the one or more biomarkers may indicate that the disease is not progressing.

Likewise, the method can also be used to monitor a subject's response to treatment. For example, one or more biomarkers such as GADD153 or Del-1 can be measure in a first biological sample at a first time point followed by treated for the disease. The one or more biomarkers can be measured in a second biological sample at a second time point to determine if the treatment is effective. Absence of, or decrease of GADD153 and an increase of Del- at the second time point compared to the first time point is indicative that the treatment is effective. No change in the one or more biomarkers may indicate that the disease is not progressing in the presence of the treatment. The treatment can be any treatment known in the art, or an experimental treatment. The treatment can include, but is not limited to, surgery, immunotherapy, administration of salivating agents such as pilocarpine, and combinations thereof.

IV. Methods of Treatment

If a subject is positive for one or more biomarkers (i.e., the presence of, or an increase in one or more Sjögren's Syndrome biomarkers in a biological sample compared to a control) the subject can be selected for treatment for Sjögren's Syndrome. Symptoms of Sjögren's Syndrome include, but are not limited to dry eyes; dry mouth; joint pain swelling and stiffness; swollen salivary glands; skin rashes or dry skin, vaginal dryness, persistent dry cough, prolonged fatigue and combinations thereof.

A. Methods of Selecting a SjöGren's Syndrome Treatment

The presence of certain biomarkers can also be used by one of skill in the art to select a particular active agent for administration to the subject. For example, if a biological sample obtained from the subject is positive for increased GADD153 expression or decreased Del-1 expression, the subject can be selected for treatment with agents known in the art for treating symptoms of Sjögren's Syndrome. Representative treatments for symptoms of Sjögren's Syndrome include, but are not limited to saliva substitutes, saliva stimulants, interferon-alpha, artificial tears, methylcellulose inserts, eye ointments, muscarinic agonist drugs, immunomodulatory drugs, and autologous serum drops.

In addition to over the counter (OTC) eye drops and mouth preparations, prescription products for dry eyes and dry mouth are available. They include Evoxac® (cevimeline), Salagen® (pilocarpine hydrochloride) and Numoisyn™ for dry mouth and Restasis® (cyclosporine ophthalmic emulsion) and Lacrisert® (hydroxypropyl cellulose ophthalmic insert) for dry eye.

B. Pharmaceutical Compositions

Pharmaceutical compositions including an active agent for treating one or more symptoms of Sjögren's Syndrome are provided. A representative active agent is Del-1 protein or biologically active fragments thereof. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration.

In preferred embodiments, the compositions are delivered directly to salivary or lacrimal cells by local injection or topical administration.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower.

1. Formulations for Parenteral Administration

In a preferred embodiment, compositions disclosed herein, including those containing active agent and optionally a delivery vehicle, are administered in an aqueous solution, by parenteral injection. The formulation may also be in the form of a suspension or emulsion. In general, pharmaceutical compositions are provided including effective amounts of an active agent, targeting moiety, and optional a delivery vehicle and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), antioxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical Administration

The active agent and optional delivery vehicle can be applied topically. Topical administration can include application to the mouth, eyes, lungs, nasal, oral (sublingual, buccal), vaginal, or rectal mucosa.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations can include penetration enhancers.

3. Oral Formulations

Oral formulations may be in the form of chewing gum, gel strips, tablets or lozenges. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

V. Devices and Kits for Detection of SjöGren's Syndrome Biomarkers in a Subject

Devices and kits for detection of Sjögren's Syndrome biomarkers in a subject are also disclosed. The marker being detected may indicate whether subject has Sjögren's Syndrome, and indicate the disease severity or progression as discussed above. The marker being detected may be a nucleic acid (or polynucleotide), protein, a carbohydrate, metabolite, as discussed above. The marker being detected can determine the format of the test (i.e., assay, strip, etc.), and/or the type of biomolecular recognition element (e.g. antibodies, antigens, lectins, etc.) being used to detect the marker. The marker being detected may be a single marker or a combination of markers. The marker being detected may be specific to one condition or multiple conditions.

There may be provided a test or support surface used for performing a test for detecting the presence of a selected marker(s). The test or support surface may be coated with/hold the selected detection antibodies, lectins etc. specific to the marker(s) being detected.

The device or kit typically includes reagents and/or apparatus that can be used to carry out the test. Some kits include an apparatus that includes a support surface for the detection of the marker. The surface, can be, for example a surface on which the selected detection antibodies, etc. can be coated/held for detection of the selected marker(s). In some embodiments, the test or support surface may be part of an assay having one or more containers (or wells). The test or support surface may be the inner surface of a well or container. The inner surface of one or more wells or containers may be coated with the detection antibody specific to the marker(s) being detected.

Any appropriate assay or ELISA (sandwich, indirect, competitive, reverse, etc.) can be provided as part of the kit or device. For example, the kits or device can provided a polystyrene microplate, having wells/containers with inner surfaces capable of being coated with antibody. These inner surfaces may or may not be treated with substances known in the art to promote or enhance coating. For example the surface can be a maxisorp, POLYSORP®, medisorp, MINISORP® or COVALINK® surface. Each well or container may be white or opaque to allow for easier visualization of any color, or any visually detectable change, occurring in or on the well or container. It will be appreciated that the size, surface area, total and/or working volumes, appearance, and/or color/visual parameters and/or qualities can be modified as desired within the scope of the present disclosure.

In some embodiments, the test or support surface may be part of a vial (or container or well), a test strip, a chromatography substrate, a gene chip, a SNAP® test, or any other diagnostic test or test system used for detecting markers. The test or support surface may be made of paper, plastic, glass, metal, etc. and take several forms such as paddle, beads, wells, electrodes, etc.

In some embodiments, non-specific adsorption to the test surfaces coated with the biomolecular recognition element (BRE), such as the coated well/container of an assay, may be minimized by blocking the test surface with a blocking agent. The blocking agent may be one or more proteins, sugars and/or polymers such as bovine serum albumin, gelatin, polyethylene glycol, sucrose, etc.

The kit or device can include an appropriate biomolecular recognition element (BRE), for detection of the biomarker. In some embodiments, the test surface is coated with the BRE (e.g., the detection antibody or lectin). The coated surface, such as the coated well/container of an assay, may be coated with a preserving (or stabilizing) agent to preserve the activity of the test surface. Test surfaces coated with the BRE and the blocking agent may also be coated with the preserving agent. The preserving agent may allow the test surfaces coated with the preserving agent, and the BRE and/or blocking agent, to be stored for an extended period of time before use. Test surfaces coated with the preserving agent, and the BRE and/or blocking agent, may maintain immunological activity for several months compared to if no preserving agent is employed (where immunological activity of a test surface coated with the BRE and/or a blocking agent may continually decline over time).

In some embodiments, the marker being detected, when present in increased or increasing amounts, may indicate a positive/reactive result. In some embodiments, the marker being detected, when absent or present in decreased or decreasing amounts, may indicate a positive/reactive result.

To detect if a marker is present in a sample, a signal from the sample may be compared against the signals of a high standard and a low standard which can be included with the kit or device. A qualitative/visual signal may be generated or visualized of the sample and test standards for making the comparison. The visual indicator may visualize or generate a signal of the sample and standards having a magnitude corresponding to the level of the marker present. The visual indicator may visualize or generate a signal for the first standard consistent with a first level of marker. The visual indicator may visualize a signal for the second standard consistent with a second level of marker.

For example, the visual indicator may visualize for the high standard a signal consistent with a level, such as the minimum level, of the biomarker in a subject with the disease or disorder. The visual indicator may visualize for the low standard a signal consistent with a level, such as the maximum level, of the biomarker in a subject without the disease or disorder. The magnitude of the signal from the biological test sample generated by the visual indicator may be compared against the standards to determine the diagnosis.

Generating the visually detectable signal can be accomplished in several ways. Any visual indicator, including any dye, chromogen, substance, substrate, or solution capable of producing a qualitative indication or visually detectable change may be utilized and included with the kit or device. The generated signal may be visually detectable with or without special equipment. For example, the signal may be a color change, or the generation of a color change along a spectrum, that is visible without special equipment. In some embodiments, it is possible to detect changes in light absorbance visually, with non-specialized light detection equipment, or specialized equipment (e.g., Spectrophotometer). In some embodiments, the signal may be detected by measuring a change in a physical or chemical property of the substrate being tested based on the presence of a label, such as an enzyme label. Types of enzyme-labeled signals known to the art include: light absorbance, light emission, fluorescence, electrochemical signal, pH, etc.

The kits and devices can include instructions for use.

In some embodiments, the kit or device is used to assaying a biological tissue samples, such as those discussed above.

EXAMPLES

Methods

Female nonobese diabetic (NOD; NOD/ShiLtJ) and control (NON/ShiLtJ) mice were purchased from the Jackson laboratory (Bar Harbor, Me.) and housed, with free access to food and water, in the laboratory animal facilities at the Georgia Regents University. The use of animals for these studies was approved by the Institutional Animal Care and Use Committee.

At 14 weeks of age, the animals were sacrificed by cervical dislocation and for procurement of the right and left submandibular and sublingual complex (thereafter referred to as salivary gland). For flow cytometry-based studies, salivary gland tissue was filtered through a cell strainer (BD Biosciences, Bedford, Mass.) and centrifuged (1500 rpm, 10 minutes) to obtain single cell suspension. On the other hand, formalin-fixed salivary tissue samples were used for immunostaining protocols (15-16, 20-22).

Analytical Flow Cytometry

Phenotypic and intracellular analyses of salivary gland cells were performed as described previously (15-16, 22). Briefly, cells were fixed and permeabilized using fix/perm concentrate (eBioScience, San Diego, Calif.) prior to incubation with antibodies for intracellular staining of interleukin (IL)-17, IL-10 (BD BioSciences, Bedford Mass.), GADD153 (Santa Cruz, Calif.), CD 19 (a B cell marker), CD3 (pan-T cell marker; Santa Cruz), CD 68 (a marker of M1 macrophages), CD206 (a marker of M2 macrophages) and Del-1 (Abcam). Then, after one wash, cells were run through a four-color flow cytometer (FACS Calibur, BD Biosciences, San Diego, Calif.) and data were collected using CellQuest™ software. Samples were double-stained with control IgG and cell markers were used to assess any spillover signal of fluorochromes; proper compensation was set to ensure the median fluorescence intensities of negative and positive cells were identical and were both gated population. Gating was used to exclude dead cells and debris using forward and side scatter plots. In each analysis, 100,000 total events were collected. As gating strategy, for each sample, isotype matched controls were analyzed in order to set the appropriate gates. For each marker, samples were analyzed in duplicate measurements. In order to minimize false positive events, the number of double positive events detected with the isotype controls was subtracted from the number of double positive cells stained with corresponding antibodies (not isotype control), respectively. Cells expressing a specific marker were reported as part of the gated events.

Assessment of Mitochondrial Membrane Potential ($\psi_m$)

Flow cytometry application of the JC-1 assay technique is used as an index of $\psi_m$ and a surrogate marker of mitochondrial permeability transition (MPT) pore opening, which is a critical event in cell death (15-16, 22). Accordingly, salivary gland cells were incubated for 15 min in the presence of 2 µM JC-1 at 37° C., 5% $CO_2$, washed twice and resuspended in DMEM ($1 \times 10^6$ cells/ml). Thereafter, labeled cells were analyzed and quantified by flow cytometry with excitation at 488 nm and emission at 530 nm (green) or 590 (red) (15-16, 22).

Assessment of Cell Death

Assessment of necrosis and apoptosis was achieved using the flow-cytometry-based Annexin V/7-Amino-Actinomycin D (7-AAD) protocol (15-16, 22) Annexin V is used to quantitatively determine the percentage of cells within a population that are actively undergoing apoptosis; 7-AAD is a standard flow cytometric viability probe and is used to distinguish viable from nonviable cells. Staining was performed according to the manufacturer's instructions (BD Biosciences, Bedford, Mass.). In brief, salivary gland cells were washed twice with cold PBS and then resuspended in Binding Buffer and gentle vortex prior to incubation with PE (Rphycoerythrin) conjugated Annexin V and 7-AAD. Cells were analyzed by flow cytometry within 1 hour after adding binding buffer. Annexin V:PE Apoptosis Detection Kit was obtained from BD Biosciences (Bedford, Mass.).

Histologic and Immunohistochemical Assessment

Tissue sections, 4 µm in thickness, were cut from formalin-fixed, paraffin-embedded salivary glands of NOD and control mice as well as from archived cases of lower lip biopsies which were documented to be consistent with Sjögren's syndrome (SS subject) and those without a diagnosis of SS. These sections were submitted for hematoxylin and eosin (H&E) staining as well as immunohistochemical staining using antibodies for 11-17 and IL-10 (Santa Cruz), GADD153, Del-1, CD19, CD3+, CD68, CD206, and caspase 3 (Abcam) according to previously described protocols (Baban, et al., *Hypertension*. 61(1):95-104 (2013); Baban, et al., *Exp Mol Pathol.*, doi:pii: S0014-4800(12)00175-X. 10.1016/j.yexmp.2012.11.004 [Epub ahead of print] (2012); Mozaffari, et al., *J Oral Pathol Med.*, 40(2):194-200 (2011); Mozaffari, et al., *J Histochem Cytochem.*, 50(4):527-32 (2002); Baban, et al., *Am J Physiol Regul Integr Comp Physiol.*, 303(11:R1136-46 (2012)).

Statistics

Data were analyzed by Student t-test with significance criteria of $p<0.05$. Data are reported as means±SEM.

Example 1

GADD153 and Del-1 are Biomarkers for SS

Figure 1B:
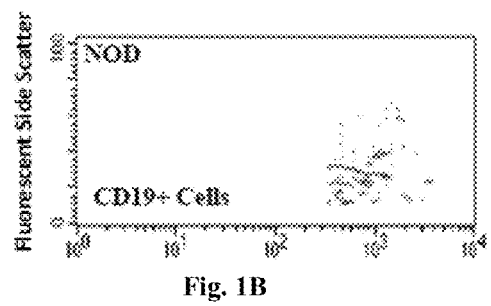
Figure 1C:
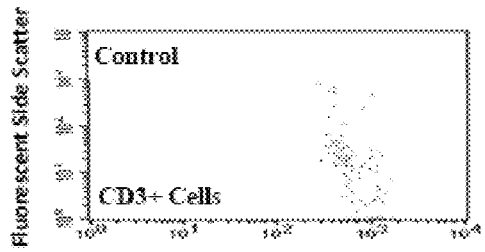
Figure 1D:
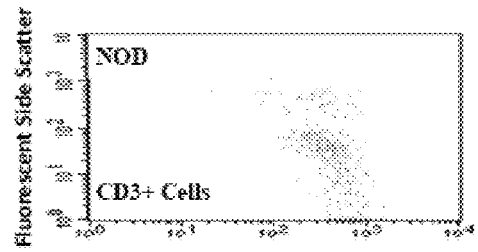
Figure 1E:
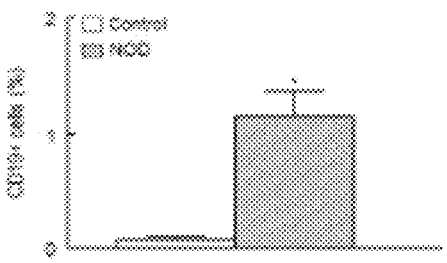
FIG. 1E is a bar graph showing the percentage of cells stained for CD19 (B cells) in the control and NOD groups, respectively, shaded according to the legend; data in the bar graph are means±SEM of 5 animals/group. The asterisk indicates a statistically significant difference (p<0.05) compared to the control group.
Figure 1F:
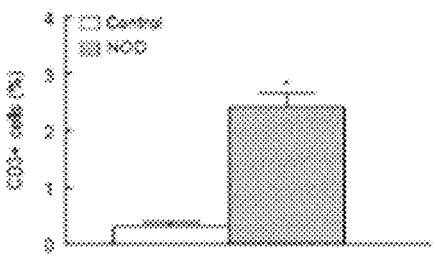
FIG. 1F is a bar graph showing the percentage of cells stained for CD3 (T cells) in the control and NOD groups, respectively (means±SEM of 5 animals/group).

A hallmark histopathological finding of SS is leukocyte infiltration of salivary glands. As expected, the NOD mice displayed foci of leukocyte infiltrates associated with loss of salivary gland parenchyma (data not shown). Subsequent flow cytometry and immunohistochemical studies showed significant increase in CD19+ and CD3+ cells in salivary gland of NOD than control mice indicative of B and T cells infiltrates (FIGS. 1A-1F). Also, salivary gland of NOD mice displayed foci of intense immunostaining for CD68, a marker of type 1 macrophages (M1) and CD206, a marker of type 2 macrophages (M2; data not shown). Importantly, leukocyte infiltration was associated with marked reduction in Del-1 positive cells of NOD salivary glands which was consistent with reduced Del-1 immunostaining of the tissue compared to the control group (FIGS. 2A-2C).

Figure 4A:
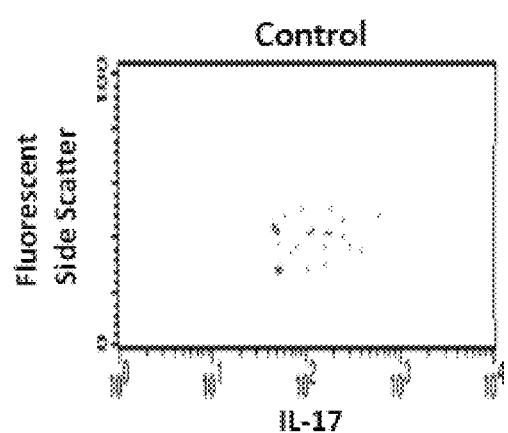
FIGS. 4A and 4B are scatter dot plots that show representative results of analytical flow cytometry, gated to exclude dead cells and debris, to visualize cells stained for IL-17 from the salivary tissue of control and NOD mice, respectively. In each analysis, 100,000 total events were collected, where each event represents a single cell or particle.
Figure 4B:
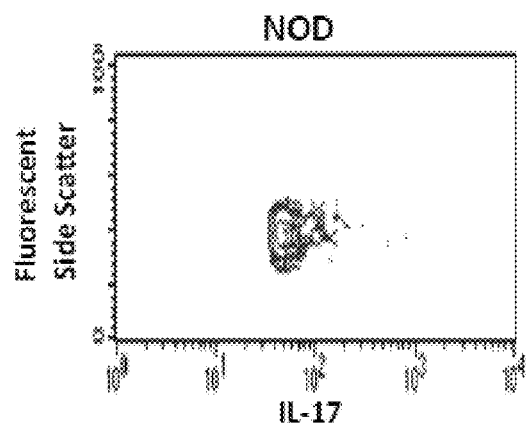
Figure 4C:
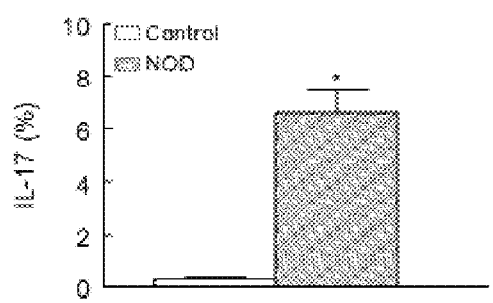
FIG. 4C is a bar graph showing the percentage of cells immunostained for IL-17 in control and NOD mice, respectively. Bars are shaded according to the legend; data in the bar graph are means±SEM of n=5 mice/group. The asterisk indicates a statistically significant difference (p<0.05) compared to the control group.
Figure 6A:
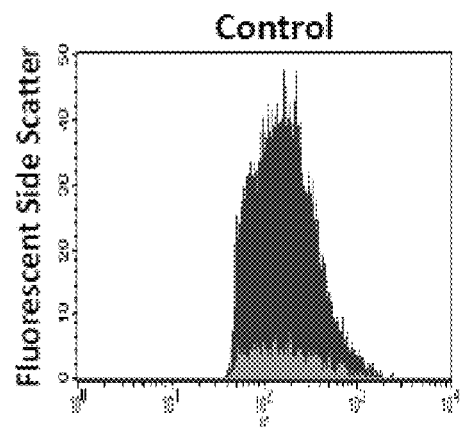
FIGS. 6A and 6B are histograms that show representative results of analytical flow cytometry, gated to exclude dead cells and debris, to visualize JC-1 monomers and JC-1 aggregates amongst cells prepared from the salivary glands of control and NOD mice, respectively.
Figure 6B:
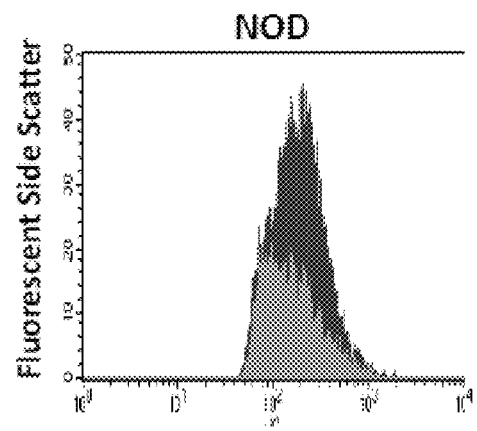
Figure 6C:
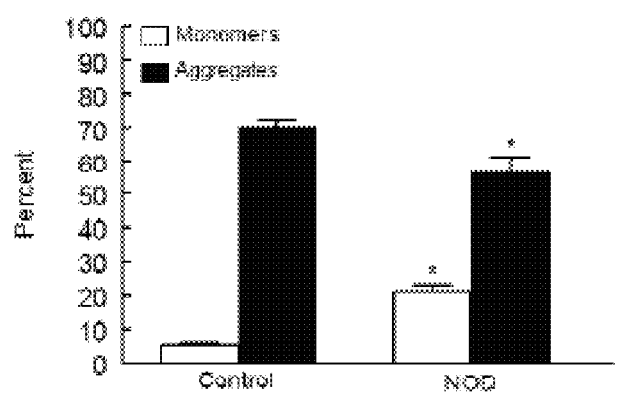
FIG. 6C is a bar graph showing the percentage of monomers and aggregates in cells from control and NOD mice, respectively. Bars are shaded according to the legend; data in the bar graph are means±SEM of n=5 mice/group. The asterisks indicate a statistically significant difference (p<0.05) compared to the control group.

Although the role of leukocyte infiltration into salivary glands in the pathogenesis of SS is indisputable, no information is available regarding the contribution of ER stress response in etiopathogenesis of SS. Thus, the expression of GADD153 was examined which is a component of DNA damage response, inflammatory cytokines and cell death. The salivary glands of NOD mice displayed foci of immunostaining for γH2AX, a sensitive marker of double stand DNA breaks (data not shown). On the other hand, FIGS. 3A-3C show that salivary gland cells of NOD mice showed significant increase in the percent of GADD153 positive cells compared to the control group. This observation is consistent with intense GADD153 immunostaining of salivary glands of NOD than control mice (FIGS. 3A-3C). While GADD153 immunostaining was rather diffuse throughout the salivary tissue, it was more intense on the luminal side of the salivary ducts. Increased GADD153 expression was associated with marked increases in percent of IL-17 positive cells but reduced IL-10 positive cells, features that were corroborated by immunohistochemistry (FIGS. 4A-4C and 5A-5C). It is noteworthy, however, that the increase in IL-17 was much more pronounced than the decline in IL-10 in salivary glands of NOD mice (FIGS. 4A-4C and 5A-5C).

Example 2

The Reciprocal Relation Between GADD153 and Del-1

Cell death in the context of mitochondrial status was examined using the flow cytometry-based JC-1 assay. As shown in FIG. 9, salivary gland cells of control mice displayed greater JC-1 aggregates, but reduced JC-1 monomers, compared to those of NOD mice. As a result, the ratio of JC-1 aggregates to monomers was significantly reduced in NOD compared to control mice suggestive of reduced $\psi_m$ and greater MPT pore opening, a determinant of cell death. FIGS. 7A-7C show representative dot matrices along with percent of cell death for each group; each dot matrix depicts necrosis (a), apoptosis/necrosis (b) and early apoptosis (c). Cells prepared from salivary glands of NOD mice displayed significantly greater percent of early apoptotic, apoptotic/necrotic and necrotic cell death. Further, immunohistochemical studies show intense staining for caspase 3 in salivary glands of NOD than control mice (data not shown).

In light of the prominent reciprocal relation between GADD153 and Del-1 in salivary glands of NOD mice, subsequent studies focused on establishing the relevance of these findings for the human condition. Accordingly, lower lip biopsy samples of subjects which were previously diagnosed with SS and those without a diagnosis of SS were subjected to immunostaining protocols for GADD153 and Del-1 (n=5 subjects per group). Microscopic examination of the H&E stained non-SS subject showed normal lobular architecture with packed mucous acini interspersed by intercalated ducts (data not shown Tissue sections on non-SS subjects were stained for DEL-1 which showed strong expression in the ductal cells as well as the periacinar myoepithelial cells (data not shown). Further, tissue sections on non-SS subjects stained for GADD153 showed minimal expression confined to the ductal cells. On the other hand, tissue sections from the SS subjects showed the typical constellation of features, two or more foci of periductal leukocytic infiltrates and acinar destruction, especially in the periductal regions (data not shown). Sections stained for DEL-1 showed significant loss of expression, when compared to the Non-SS subject, with minimal staining confined to some of the ductal structures, and complete lack of expression in the periacinar myoepithelial cells (data not shown). On the other hand, tissue sections stained for GADD153 showed upregulation, when compared to the non-SS subject, with strong expression in the ductal cells and minimal expression by some of the periacinar myoepithelial cells (data not shown). Thus, the reciprocal relation between GADD153 and Del-1 in salivary glands of NOD mice (FIGS. 2A-2C and 3A-3C) is also a feature of lower lip biopsy samples of SS subjects (data not shown).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of diagnosing and treating one or more symptoms of Sjögren's Syndrome in a subject comprising:
   measuring the level of growth arrest and DNA damage-inducible protein GADD153 (GADD153) and developmental endothelial locus-1 Del-1 (Del-1) in a biological sample obtained from the subject and comparing it to a control,
   wherein the biological sample is selected from the group consisting of tears, saliva, salivary gland tissue, blood, serum, and plasma,
   wherein an increase in GADD153 expression in the biological sample of the subject and a decrease in Del-1 expression in the biological sample of the subject compared to the control is indicative that the subject has Sjögren's Syndrome; and
   administering one or more therapeutic compositions selected from the group consisting of saliva substitutes, saliva stimulants, interferon-alpha, artificial tears, methylcellulose inserts, eye ointments, muscarinic agonist drugs, immunomodulatory drugs, and autologous serum drops in an amount effective to treat one or more symptoms of Sjögren's Syndrome in the subject having gren's Syndrome.

2. The method of claim 1, further comprising the step of measuring the amount of interleukin-10 in the salivary glands of the subject, wherein a statistically significant reduction of IL-10 in the salivary glands of the subject is indicative that the subject has Sjögren's Syndrome.

3. The method of claim 1, further comprising the step of measuring the amount of interleukin-17 (IL-17) in the salivary glands of the subject, wherein a statistically significant increase in IL-17 in the salivary glands of the subject is indicative that the subject has Sjögren's Syndrome.

4. The method of claim 1, further comprising the step of detecting a disruption in $\psi_m$ in association with a statistically significant increase in both apoptosis and necrosis accompanied by caspase 3 activation, wherein a disruption in $\psi_m$ in association with a statistically significant increase in both apoptosis and necrosis accompanied by caspase 3 activation is indicative that the subject has Sjögren's Syndrome.

5. A method of diagnosing and treating one or more symptoms of Sjögren's Syndrome in a subject comprising:
   assaying a biological sample obtained from the subject for:
   (a) levels of GADD153, Del-1, IL-10, IL-17 and disruption in $\psi_m$ in association with a statistically significant increase in both apoptosis and necrosis accompanied by caspase 3activation in the biological sample of the subject, wherein
      (1) a statistically significant decrease in Del-1,
      (2) a statistically significant increase in GADD153,
      (3) a statistically significant reduction of IL-10,
      (4) a statistically significant increase in IL-17, and
      (5) a disruption in $\psi_m$ in association with a statistically significant increase in both apoptosis and necrosis accompanied by caspase 3 activation
   compared to the control is indicative that the subject has Sjögren's Syndrome, wherein the biological sample is selected from the group consisting of tears, saliva, salivary gland tissue, blood, serum, and plasma;
   and administering and effective amount of Del-1 to treat one or more symptoms of Sjögren's Syndrome in the subject having Sjögren's Syndrome.

* * * * *